US007057164B2

(12) United States Patent
Springsteen et al.

(10) Patent No.: US 7,057,164 B2
(45) Date of Patent: Jun. 6, 2006

(54) REFERENCE STANDARD AND METHOD FOR CALIBRATION

(75) Inventors: Arthur Springsteen, Wilmington, OH (US); Ian A. Cowe, Osbaldwick (GB)

(73) Assignee: Foss Analytical AB, Hoganas (SE)

( * ) Notice: Subject to any disclaimer, the term of this patent is extended or adjusted under 35 U.S.C. 154(b) by 283 days.

(21) Appl. No.: 10/659,745

(22) Filed: Sep. 11, 2003

(65) Prior Publication Data

US 2004/0262510 A1 Dec. 30, 2004

(30) Foreign Application Priority Data

Jun. 27, 2003 (SE) .................................. 0301897

(51) Int. Cl.
*G12B 13/00* (2006.01)

(52) U.S. Cl. .................................. 250/252.1; 378/207

(58) Field of Classification Search ............ 250/252.1, 250/353, 338.1, 343, 428, 461.1, 461.2, 459.1; 356/243.5; 378/207
See application file for complete search history.

(56) References Cited

U.S. PATENT DOCUMENTS

| | | | | |
|---|---|---|---|---|
| 3,478,210 A | * | 11/1969 | Janacek | 250/428 |
| 4,184,768 A | * | 1/1980 | Murphy et al. | 356/326 |
| 4,465,929 A | * | 8/1984 | Edgar | 250/252.1 |
| 4,761,552 A | * | 8/1988 | Rosenthal | 250/252.1 |
| 4,866,644 A | * | 9/1989 | Shenk et al. | 356/319 |
| 5,534,698 A | * | 7/1996 | Ohshima et al. | 250/339.11 |
| 5,637,505 A | * | 6/1997 | Li et al. | 436/8 |
| 5,689,110 A | * | 11/1997 | Dietz et al. | 250/252.1 |
| 5,892,229 A | * | 4/1999 | Crozier et al. | 250/339.13 |
| 5,933,792 A | * | 8/1999 | Andersen et al. | 702/32 |
| 5,936,727 A | * | 8/1999 | Trygstad | 356/243.5 |
| 6,358,860 B1 | * | 3/2002 | Scheer et al. | 438/745 |
| 6,470,279 B1 | * | 10/2002 | Samsoondar | 702/28 |
| 6,471,916 B1 | * | 10/2002 | Noblett | 422/82.08 |
| 6,956,203 B1 | * | 10/2005 | Staton et al. | 250/252.1 |
| 2004/0084612 A1 | * | 5/2004 | Staton et al. | 250/252.1 |

FOREIGN PATENT DOCUMENTS

| | | |
|---|---|---|
| EP | 0 368 436 | 5/1990 |
| EP | 0 906 936 | 4/1999 |
| EP | 0 959 353 | 11/1999 |

\* cited by examiner

OTHER PUBLICATIONS

I. Yasunobu; *Patent Abstracts of Japan;* "Phantom for Optical Scanning Device"; Publication No. 03-146850; 1991.

*Primary Examiner*—David Porta
*Assistant Examiner*—Faye Polyzos
(74) *Attorney, Agent, or Firm*—Browdy and Neimark, PLLC

(57) ABSTRACT

The present invention provides a reference standard for calibration of an analysis instrument. The reference standard comprises a solid body formed of a number of compounds and a substrate having scattering properties similar to a product to be analyzed with said analysis instrument and being spectrally neutral in a wavelength range to be used in the analysis instrument. The substrate and the compounds in combination with respect to intensity, wavelength and scattering properties imitate the spectral response of the product to be analyzed with said analysis instrument. The present invention also provides a method for calibration of an analysis instrument, which method comprises recording, by means of said analysis instrument, the spectral response of a reference standard comprising a solid body, which with respect to intensity, wavelength and scattering properties imitates the spectral response of a product to be analyzed with said analysis instrument; evaluating the differences between the response from said analysis instrument and an expected spectral response; and calibrating said analysis instrument according to the result of the evaluation.

19 Claims, 2 Drawing Sheets

REFERENCE STANDARD AND METHOD FOR CALIBRATION

TECHNICAL FIELD OF THE INVENTION

The invention relates to a reference standard and a method for calibration of an analysis instrument.

BACKGROUND OF THE INVENTION

Reference standards are widely used in visible and near infrared spectroscopy to ascertain proper performance of analysis instruments. The accuracy of the instruments in analyzing and identifying materials depends upon the accuracy with which the wavelengths and intensity of the radiation within the wavelength range to be used in the analysis instrument are known. The very capability of the instrument to measure properties of different products is dependent upon this accuracy. For this reason, there is a need to verify with precision that the calibration of the instrument is correct for the wavelength range to be used in the instrument.

Typically, two types of reference standards are used. Intensity standards are used to set and check that the detector accurately detects the intensity of the radiation and wavelength standards are used to check that the wavelength scale of the instrument is accurate. An example of a wavelength standard is shown in U.S. Pat. No. 5,936,727.

Analysis instruments can be calibrated along the intensity scale with transmittance screens or filters and reflectors of neutral density. The instrument is then calibrated to correct discrepancies between the detected intensity and an expected intensity result. In U.S. Pat. No. 4,761,552 a reference standard that is used for reflectance calibration of an instrument is disclosed.

Calibration along the wavelength scale is made by using emission lines from arc sources such as deuterium or xenon, or absorption bands from polymer films such as polystyrene or from rare earth oxide doped materials. The wavelength of the emission line is well-defined. Therefore, a wavelength scale may suitably be calibrated using these emission lines as adjusters of the wavelength scale.

However, the current technology for ensuring calibration with respect to intensity and wavelength is not satisfactory to ensure adequate matching between instruments, quality control of the instruments or performance validation of the instruments. Calibration is impaired by the fact that measurements of a product to be analyzed are not well characterized by intensity measurements that take no account of the scattering properties or physical nature of the product.

One attempt to remedy this inadequacy is to use natural products as reference standards, i.e. each reference standard is made of the respective product to be analyzed on the analysis instrument. However, these reference standards lack temporal and mechanical stability and therefore have a short lifetime, requiring great care in the handling of the reference standards to minimize spectral changes between two sets of measurements. Consequently, these reference standards are inadequate in use, especially across large geographical areas. The usage of such reference standard is shown in U.S. Pat. No. 4,866,644.

SUMMARY OF THE INVENTION

It is an object of the invention to provide an improved reference standard for calibration of an analysis instrument.

It is another object of the invention to provide a reference standard that has adequate temporal and mechanical stability, while providing adequate calibration of analysis instrument.

It is a further object of the invention to provide a method for improved calibration of an analysis instrument.

The objects are achieved by a reference standard according to claim 1 and by a method according to claim 10. Embodiments are defined by the dependent claims 2–9 and 11–20.

Thus, the invention provides a reference standard for calibration of an analysis instrument. The reference standard comprises a solid body formed of a number of compounds and a substrate having scattering properties similar to a product to be analyzed with said analysis instrument and being spectrally neutral in a wavelength range to be used in the analysis instrument. The substrate and the compounds in combination imitate, with respect to intensity, wavelength and scattering properties, the spectral response of the product to be analyzed with said analysis instrument.

As a result of the invention an improved reference standard for calibration of an analysis instrument is provided. Since the reference standard is made of compounds in a solid body the reference standard is stable over a long period of time and is also insensitive to changes caused by for example mechanical vibration, shock temperature changes, humidity changes or biological or chemical degradation. Since the reference standard imitates the spectral response of a product to be analyzed, it is possible to perform a calibration of the intensity at every wavelength within the wavelength range that is used. Due to the properties of the standard, the calibration is performed, at each wavelength, in relation to a standard that imitates the response for a product to be analyzed at that particular wavelength. Thus, a spectral measurement of the standard will, by the nature of the standard, give a reference spectrum that may be used over all wavelengths for calibrating the analysis instrument. Thus, the reference standard has an advantage of giving rise to a possibility to detect small important variations in the intensity when analyzing a product on the analysis instrument calibrated by means of the reference standard. These small variations may contain the information that is important when analyzing the product and without this possibility they may be invisible in the analysis.

Further, the scattering properties will affect the amount of light outputted in different directions. As a result, different instruments, and particularly instruments which collect light with different optical geometry, can give greatly different spectral responses depending on the scattering properties of the sample being measured. Using a standard that imitates the scattering properties of the product to be analyzed will therefore greatly enhance the calibration.

An ideal material is a perfectly lambertian scatterer. That is, the reflectance is independent of the illumination or viewing angle. No materials are perfectly lambertian, however a standard being very close to a perfect lambertian scatterer will often well imitate a natural product. Many natural samples, such as sugar, meal, or ground forage, also come close to being perfect lambertian scatterers, as do many diffusely transmitting samples such as meat or dairy products.

According to an embodiment of the invention, the reference standard is highly lambertian. This behavior makes the reference standard less sensitive to instrument geometry and thereby ensures that there will be little variation in response from instrument to instrument if these instruments have identical or near-identical geometry. The objects of the invention are also achieved by a method for calibration of an analysis instrument. The method comprises recording, by means of said analysis instrument, the spectral response of a reference standard comprising a solid body, which with respect to intensity, wavelength and scattering properties imitates the spectral response of a product to be analyzed with said analysis instrument; evaluating the differences between the spectral response from said analysis instrument and an expected spectral response and calibrating said analysis instrument according to the result of the evaluation.

By using a reference standard that, with respect to intensity, wavelength and scattering properties imitates the spectral response of a product to be analyzed on the analysis instrument the possibility to carry out a better calibration of the analysis instrument is improved since the analysis instrument may be calibrated with respect of both intensity and wavelength with the same reference standard.

In the context of this application, the phrase "spectrally neutral within a wavelength range" should be construed as an absorbance that is essentially constant within that wavelength range. There may be a minor slope in the absorbance over the wavelength range that constitutes a difference of less than 10 percent. However, there are no absorbance peaks or any other strong dependence between the absorbance and wavelength. Further, the term "spectral response" denotes an intensity profile over a wavelength range as a result of irradiation.

According to an embodiment of the invention, a compound imitates the spectral response of a physical property of the product to be analyzed. A physical property may be one in the group of moisture, protein content, fat content, oil content, optical density, fiber content, starch content, sugar content and wavelength markers. By having a number of compounds together in the reference standard that each imitates a spectral response of a specific physical property, the spectral response of a product in the wavelength range to be used in the analysis instrument may be imitated.

According to another embodiment, at least one of the compounds is inorganic. Inorganic compounds usually are more stable than organic compounds and therefore using inorganic compounds makes the reference standard even more temporally stable.

According to a further embodiment, the substrate is a fluorinated substrate. The substrate may be polytetrafluoroethylene (PTFE). PTFE has an essentially constant absorbance over a very broad range of wavelength. Further, the absorbance is very weak and there are no absorbance peaks. This makes PTFE a good material to use as a substrate in the solid body. PTFE is also a material that is suitable for compression which allows a solid body to be formed together with the different compounds.

According to another embodiment, the compounds in the solid body are homogeneously distributed within the solid body. Thus, the spectral response is the same independently of where on the reference standard the recording of the spectral response is made. Thus, the compounds being homogeneously distributed within the solid body makes a recording of the spectral response insensitive to the positioning of the reference standard.

According to yet another embodiment, the substrate may be spectrally neutral in the visible and near infrared region. The substrate may be spectrally neutral in only a part of the visible and near infrared region. It may even be spectrally neutral in the ultra violet region or parts thereof. It is also possible that the substrate is spectrally neutral in the mid-infrared region. For the purpose of calibration of the analysis instrument, it is only of importance that the substrate is spectrally neutral in the wavelength range used when analyzing the product with the analysis instrument.

Further, the product to be analyzed may be one in the group of feed, forage, grain, flour, meal, protein extracts, derived agricultural products, sugar, sweeteners, meat and dairy products. Thus, the reference standard is formed imitating the spectral response of one of these products that is to be analyzed with the analysis instrument. Consequently, the analysis instrument is thereby calibrated by means of said reference standard making the instrument optimally prepared for analyzing that specific product.

According to one embodiment the product to be analyzed is a pharmaceutical product.

According to an embodiment of the inventive method, the expected spectral response is obtained by recording, by means of a reference instrument, the spectral response of said reference standard. The reference instrument is carefully controlled to always record a correct spectral response. In this way, the recording will give the correct spectral response and therefore it may be used as the expected spectral response.

According to another embodiment of the inventive method, the reference instrument is a master instrument. Further, the analysis and reference instruments may be spectrometers.

According to a further embodiment of the inventive method, recording comprises irradiating said reference standard with electromagnetic radiation and spectrally detecting the electromagnetic radiation which has been transmitted through or reflected from said reference standard. A spectral response of a reference standard is in other words obtained by irradiating the reference standard with electromagnetic radiation and detecting the radiation that either is transmitted through or reflected from the reference standard. Whether the detected radiation is the transmitted radiation or the reflected radiation depends on which kind of analysis instrument that is used, i.e. if the analysis instrument is an instrument that detects the radiation transmitted through the reference standard or the radiation reflected from the reference standard. In either case the spectral response is an intensity profile over a wavelength range as a result of the irradiation.

According to yet another embodiment of the inventive method, the method comprises transforming the spectral response from the analysis instrument and the expected spectral response into factor space based on the properties of the product to be analyzed on the analysis instrument. In order to transform the spectral responses into factor space, a factor analysis has to be made. This factor analysis is used to extract the features in the spectral response that are of importance and thereby easily discard noise in the system that is of no importance to the evaluation.

Further, evaluating may comprise directly comparing the spectral response from said analysis instrument with the expected spectral response. In this case, the spectral responses do not have to be transformed.

Alternatively, evaluating may comprise mathematical prediction of a set of parameters from an equation predicting composition.

As a further alternative, evaluating comprises comparing the spectral response from said analysis instrument with the expected spectral response in factor space. Thus, only the features that are of importance in the spectral responses is compared. As a result, the calibration will not make corrections to the analysis instrument that are due to noise or other reasons, which are not common to all measurements and therefore should not form part of the corrections.

According to another embodiment of the inventive method, recording comprises irradiating the reference standard with electromagnetic radiation and scanning said radiation over wavelengths within the range of visible and near infrared light. The radiation may also be scanned over wavelengths within the ultra violet or mid-infrared region. The wavelength range is chosen depending on the wavelength range that is suitable when analyzing a specific product on the analysis instrument. It is of course also dependent on what analysis instrument is used.

Finally, recording the spectral response of a reference standard may comprise recording the spectral response of a reference standard that comprises a solid body formed of a number of compounds and a substrate having scattering properties similar to a product to be analyzed with said analysis instrument and being spectrally neutral in a wavelength range to be used in said analysis instrument, wherein the substrate and the compounds in combination with respect to intensity, wavelength and scattering properties imitate the spectral response of a product to be analyzed with said analysis instrument. As a result, a reference standard that is stable over a long period of time and insensitive to various other changes is used.

BRIEF DESCRIPTION OF THE DRAWINGS

Other features and advantages of the present invention will become apparent from the following detailed description of a presently preferred embodiment. The description is made with reference to the accompanying drawings, which by way of example show an embodiment of the invention.

DETAILED DESCRIPTION OF A PRESENTLY PREFERRED EMBODIMENT

Figure 1:
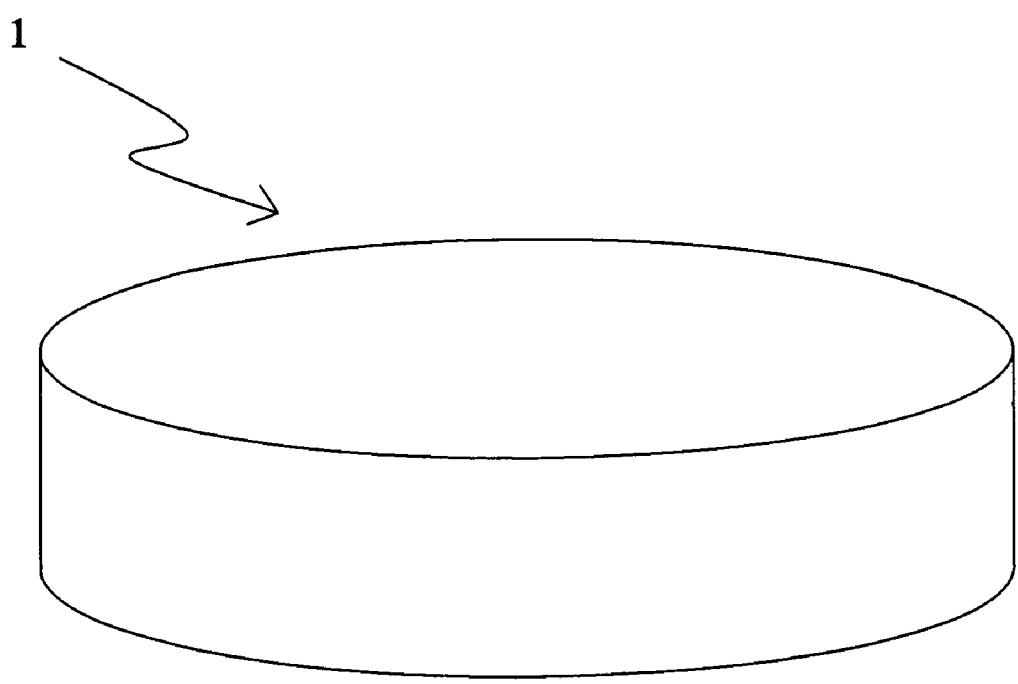
FIG. 1 is a schematic view of a reference standard according to an embodiment of the invention.

Referring to FIG. 1, a reference standard for calibration of an analysis instrument will now be described. The reference standard comprises a solid body 1 that is formed of a number of compounds and a substrate. The substrate is spectrally neutral in a wavelength range to be used in the analysis instrument and has scattering properties that are similar to a product to be analyzed with the analysis instrument. The substrate and the combination of compounds imitate, with respect to intensity, wavelength and scattering properties, the spectral response of a product to be analyzed with the analysis instrument.

The solid body is formed by mixing, under high shear, the substrate with one or more inorganic and/or organic compounds. The resultant homogeneous body is then subjected to sufficient pressure to cause the mixture to coalesce into a single highly compressed body, i.e. the solid body. The substrate and the compounds are provided in the form of powder, which is then pressed into forming the solid body.

According to the preferred embodiment, the substrate which embeds the compounds in the solid body is PTFE. PTFE is suitable material, because it has appropriate absorbance features. The absorbance of PTFE is essentially constant over a very broad wavelength range. Further, the absorbance is very weak and PTFE lacks absorbance peaks. The strongest absorbances which might interfere with the absorbances of the compounds only occur at longer wavelengths leaving most of the near infrared and the visible spectrum free from interference. The PTFE material, besides having low absorbance, is highly scattering in the optical sense. This characteristic gives the material high reflectance. Moreover, during light penetration through the material, the light will very often be scattered internally and if the material is thin enough, light will be transmitted through the material. The PTFE may be thought of as a diluent and a binder which holds the compounds in place. Further, the optical properties of the PTFE permit it to reflect or transmit light with practically no absorption of visible or near infrared light while permitting the light to interact with the compounds in the solid body.

While PTFE is a preferred material of the substrate, other materials may be used. Specifically, any perhalopolyethylene may be used, such as poly(perchlorethylene) or poly(per(chlorofluoro)ethylene) or poly(chlorotrifluorethylene) may be used. As another variation a monomer, per(chlorofluoro)ethylene, can be copolymerized with tetrafluorethylene to provide the powder from which the solid body is formed. Generally, any solid polymeric material that contains no bonds between hydrogen and carbon, oxygen or nitrogen, would provide a solid body which would be a highly suitable substitute for PTFE. In such a polymer, the backbone of the polymer chain contains only carbon. However, it is possible for the polymer chain to include other atoms such as oxygen as long as the oxygen or other atom is bonded only to carbon and is not bonded to any other element such as hydrogen. Examples of such materials based on tetrafluorethylene oxide and perfluorethylene oxide are: poly(tetrafluorethylene oxide-co-difluoromethylene oxide); poly(tetrafluorethylene-co-tetrafluorethylene perfluoropropyl ether); and poly(perfluoropropylene oxide-co-perfluoroformaldehyde). Many halogenated polymers exist which are related to those described above, but which are not perhalogenated. Such polymers, called hydrohalo polymers, can be prepared from monomers which contain some hydrogen as well as halogen, e.g., vinylidene chloride, $CH_2Cl_2$, or vinylidene fluoride, $CH_2CF_2$. Alternatively, hydrohalo polymers can be prepared through copolymerization of monomers containing no halogen, such as ethylene, and monomers that are perhaolgenated, such as tetrafluorethylene. Such materials would be sparsely populated with CH bonds which will absorb in the infrared and near infrared region, but the absorptivities of such materials are reduced compared to those in their pure hydrocarbon counterparts due to the effects caused by the presence of fluorine or simply dilution. While such materials have significantly stronger absorbance than PTFE, they nevertheless could be useful as a solid body material. For such materials to have a practical utility as a solid body in a reference standard, the frequency of occurrence of the C—H bonds in the material must be low enough that at least half of the absorbance peaks caused by the compounds in the solid body remain substantially unshifted in wavelength and unobscured.

The compounds to be used in the forming of the solid body may be chosen in dependence on what spectral response is to be achieved. Thus, a combination of compounds is chosen in order to imitate the spectral response of a certain product. The combination of compounds may be varied to a large degree depending on what product is to be imitated. Each compound in a combination may be chosen to imitate a specific property of the product. In the following, examples of compounds that may be used to imitate specific properties are given. Using these compounds, a combination may be composed to imitate the spectral response of a product.

To imitate moisture in the reference standard, the following compounds may be used: stable hydrates of inorganic salts, such as magnesium sulfate dihydrate, sodium sulfate decahydrate, copper sulfate pentahydrate, and aluminium trihydrate. Further, stable organic molecules may be used, such as ascorbic acid, salts of ascorbic acid, and other stable organic molecules with sufficient hydroxyl groups to imitate moisture in spectral responses.

To imitate protein in the reference standard, stable proteins, such as gluten from wheat or corn, albumen, casein, and other stable naturally occurring proteins may be used. Further, polymeric and monomeric materials that contain amide linkages, such as those found in Nylon-6, and Nylon-66, other stable amide containing polymers, and monomers, such as acetamide and related stable, solid amides and amino acids, may be used.

Fat or oil may be imitated in the reference standard by using metal salts of fatty acids such as sodium, magnesium, calcium or other alkali or alkaline metal salts of stearic, palmitic, lauric, myristic, and other saturated or unsaturated fatty acids.

Optical density may be imitated in the reference standard by carbon black, lamp black, 'bone black', graphite and ligneous materials.

To imitate fiber purified cellulose, hemi-cellulose, cotton lint, dried paper or wood pulp may be used. Starch may be imitated by using corn, rice, wheat, and other starches.

Wavelength markers may be created in the reference standard by using rare earth oxides, polystyrene powder, talc or any material that exhibits sharp absorbance band(s) in the wavelength range to be used in the analysis instrument.

Using the different compounds, a reference standard that imitates the spectral response of, for example wheat, may be formed by using a combination of compounds that consists of: gluten for imitating and adjusting the protein level, calcium sulfate dihydrate for imitating and adjusting the moisture level and cellulose for imitating and adjusting the fiber level. The substrate used should be PTFE and the preferred wavelength range to use when recording the spectral response is the visible and near infrared region, which is usually used when analyzing wheat.

Such reference standards may in similar ways be formed for imitating the spectral response of feed, forage, grain, flour, meal, protein extracts, derived agricultural products, sugar, sweeteners, meat or dairy products.

The ultra violet region ranges from about 200 nm to about 380 nm, the visible region ranges from about 380 nm to about 780 nm, near infrared region ranges from about 780 nm to about 2500 nm and mid-infrared ranges from about 2500 nm to about 25000 nm.

Figure 2:
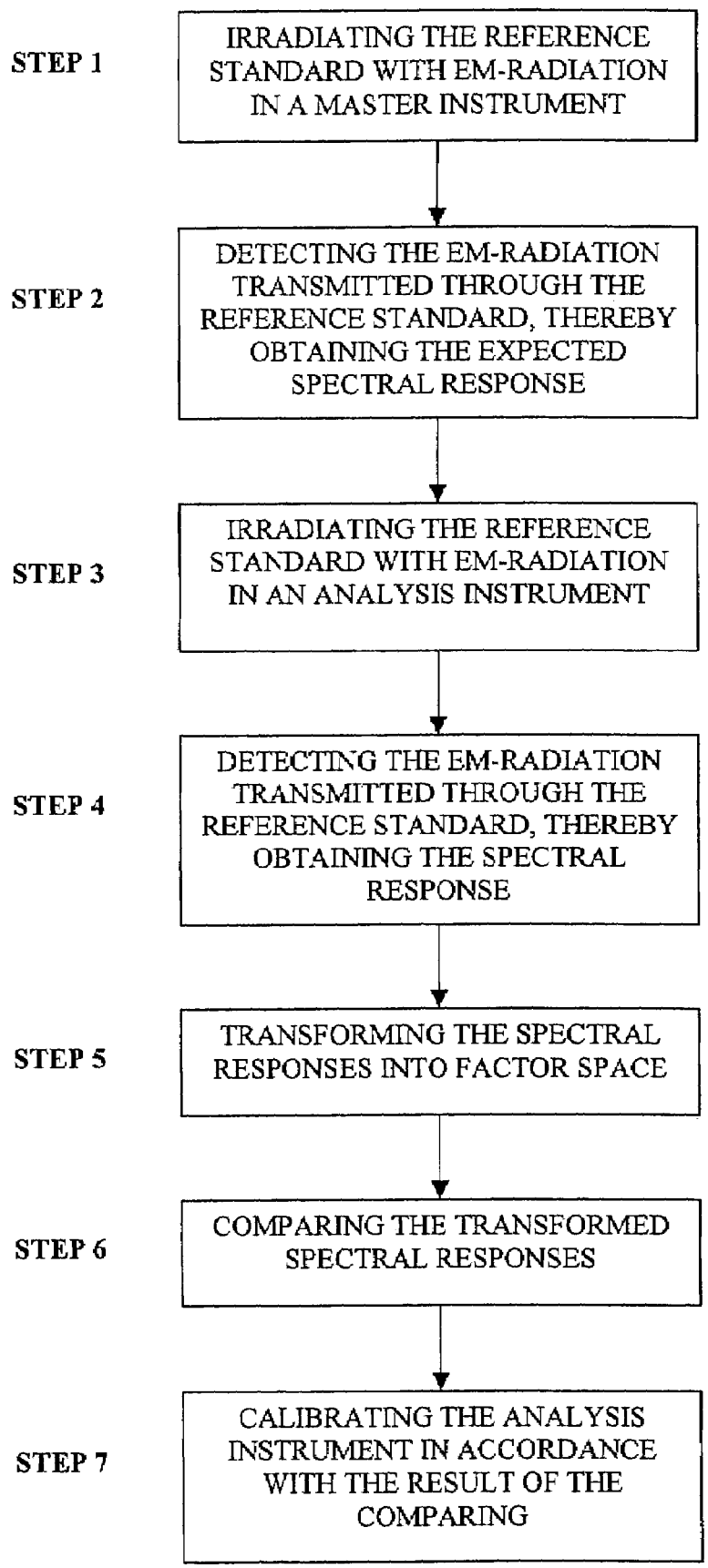
FIG. 2 is a flow chart of a method for calibration of an analysis instrument according to an embodiment of the invention.

Referring to FIG. 2, a method for calibration of an analysis instrument will now be described. The wavelengths used may be within the range of ultra violet light, visible light, near infrared light and mid-infrared light. The wavelengths used may of course be only a part of any of these ranges of light mentioned. In the embodiment described in the following, the radiation is scanned over the wavelengths within the range of visible and near infrared light.

The reference standard is placed in a master instrument. Thereafter, it is irradiated with electromagnetic radiation, step 1, which is scanned over wavelengths within the range of visible and near infrared light.

Next, the electromagnetic radiation that is transmitted through the reference standard is spectrally detected, step 2, thereby obtaining the expected spectral response. Alternatively, the expected spectral response is obtained by detecting the electromagnetic radiation that is reflected from the reference standard. Which type of radiation that is detected depends on the type of analysis instrument that is used. The master instrument is carefully controlled in order to detect a correct spectral response. These two steps only have to be made once for every reference standard. Throughout its entire lifetime the reference standard should have the same expected spectral response. Therefore the expected spectral response should not have to be recorded more than once. The recording of the expected spectral response is often performed at the premises of the manufacturer of the reference standard, since that is where the master instrument often is located. Thus, once the expected spectral response has been obtained it is used as long as the reference standard is used. The rest of the steps, described below, are on the other hand performed on the analysis instrument, which may be placed anywhere in the world.

Next, the reference standard is placed in the analysis instrument that is to be calibrated. Then, the reference standard is irradiated with electromagnetic radiation, step 3, which is scanned over wavelengths with in the same range as in the master instrument, i.e. visible and near infrared light. In order to enable comparison between the spectral response from the analysis instrument and the expected spectral response, the same wavelengths have to be used in the master instrument and in the analysis instrument that is to be calibrated.

Next, the electromagnetic radiation that is transmitted through or reflected from the reference standard is spectrally detected, step 4, thereby obtaining the spectral response. Whether it is the transmitted or reflected radiation that is spectrally detected with the analysis instrument depends on how the expected spectral response is detected with the master instrument. The spectral response from the analysis instrument and the expected spectral response from the master instrument have to be detected in the same way in order to enable comparison between these spectral responses.

Further, the spectral response from the analysis instrument and the expected spectral response is transformed into factor space, step 5. The transformed spectral responses are thereafter compared, step 6.

Step 5 does not have to be performed. Instead, the spectral responses may be used as they are for the comparison. The spectral response from the analysis instrument may then be directly compared with the expected spectral response without any transformation of the spectral responses being made. Alternatively, a mathematical prediction of a set of parameters from an equation predicting composition may be used. Such predicted parameters may be derived from regression models based on multiple linear regression or wavelength values, principal component scores, partial least square scores or scores derived from calculations undertaken by artificial neural networks or some similar mathematical modeling process.

Finally, the analysis instrument is calibrated in accordance with the result of the comparing, step 7. The calibration may then be performed on both the wavelength scale and on the intensity scale. Since the spectral response with respect to intensity and wavelength imitate the spectral response of a product both the wavelength-scale and the intensity-scale are calibrated at the same time. This implies that corrections to the intensity-scale may be performed only at a part of the wavelength-scale. Further, different corrections to the wavelength-scale may be performed in different parts of the wavelength-scale. Thus, non-linear calibrations are possible. As a result, calibration of the analysis instrument may be more accurately controlled and thereby improved.

It should be emphasized that the embodiments described herein are in no way limiting and that many alternative embodiments are possible within the scope of protection defined by the appended claims.

For example, the recording of the spectral response on the analysis instrument may be performed before the expected spectral response is recorded on the master instrument.

The invention claimed is:

1. A reference standard for calibration of an analysis instrument, said reference standard comprising
   a solid body formed of a number of solid compounds and a solid substrate,
   the substrate having scattering properties similar to a product to be analyzed with said analysis instrument and being spectrally neutral in a wavelength range to be used in the analysis instrument,
   wherein the substrate and the compounds in combination imitate, with respect to intensity, wavelength and scattering properties, the spectral response of the product to be analyzed with said analysis instrument.

2. The reference standard according to claim 1, wherein a compound imitates the spectral response of a physical property of the product to be analyzed, which physical property is one in the group of moisture, protein content, fat content, oil content, optical density, fiber content, starch content, sugar content and wavelength markers.

3. The reference standard according to claim 1, wherein said substrate is polytetrafluoroethylene (PTFE).

4. The reference standard according to claim 1, wherein said substrate is spectrally neutral in the visible and near infrared region.

5. The reference standard according to claim 1, wherein the product to be analyzed is one in the group of feed, forage, grain, flour, meal, protein extracts, derived agricultural products, sugar, sweeteners, meat and dairy products.

6. The reference standard according to claim 1, wherein the product to be analyzed is a pharmaceutical.

7. A method for calibration of an analysis instrument, said method comprising
   recording, by means of said analysis instrument, the spectral response of a reference standard according to claim 1, which with respect to intensity, wavelength and scattering properties imitates the spectral response of a product to be analyzed with said analysis instrument,
   evaluating the differences between the spectral response from said analysis instrument and an expected spectral response,
   calibrating said analysis instrument according to the result of the evaluation.

8. The method according to claim 7, wherein the expected spectral response is obtained by recording, by means of a reference instrument, the spectral response of said reference standard.

9. Method according to claim 8, wherein the reference instrument is a master instrument.

10. Method according to claim 8, wherein the analysis and reference instruments are spectrometers.

11. The method according to claim 7, wherein recording comprises irradiating said reference standard with electromagnetic radiation and spectrally detecting the electromagnetic radiation which has been transmitted through or reflected from said reference standard.

12. The method according to claim 7, wherein the method further comprises transforming the spectral response from the analysis instrument and the expected spectral response into factor space based on the properties of the product to be analyzed on the analysis instrument.

13. The method according to claim 7, wherein the evaluating comprises directly comparing the spectral response from said analysis instrument with the expected spectral response.

14. The method according to claim 7, wherein the evaluating comprises mathematical prediction of a set of parameters from an equation predicting composition.

15. Method according to claim 7, wherein recording comprises irradiating the reference standard with electromagnetic radiation and scanning said radiation over wavelengths within the range of visible and near infrared light.

16. Method according to claim 7, wherein recording the spectral response of a reference standard comprises recording the spectral response of a reference standard that comprises a solid body formed of a number of compounds and a substrate having scattering properties similar to a product to be analyzed with said analysis instrument and being spectrally neutral in a wavelength range to be used in said analysis instrument, wherein the substrate and the compounds in combination with respect to intensity, wavelength and scattering properties imitate the spectral response of a product to be analyzed with said analysis instrument.

17. A reference standard for calibration of an analysis instrument, said reference standard comprising
   a solid body formed of a number of compounds and a substrate having scattering properties similar to a product to be analyzed with said analysis instrument and being spectrally neutral in a wavelength range to be used in the analysis instrument,
   wherein the substrate and the compounds in combination, with respect to intensity, wavelength and scattering properties, imitate the spectral response of the product to be analyzed with said analysis instrument, and
   wherein at least one of the compounds is inorganic, or said substrate is a fluorinated substrate, or the compounds in the solid body are homogeneously distributed within the solid body.

18. A method for calibration of an analysis instrument, said method comprising
   recording, by means of said analysis instrument, the spectral response of a reference standard comprising a solid body, which with respect to intensity, wavelength and scattering properties imitates the spectral response of a product to be analyzed with said analysis instrument,
   evaluating the differences between the spectral response from said analysis instrument and an expected spectral response,
   calibrating said analysis instrument according to the result of the evaluation,
   wherein the evaluating comprises comparing the spectral response from said analysis instrument with the expected spectral response in factor space.

19. Method according to claim 18, wherein recording comprises irradiating the reference standard with electromagnetic radiation and scanning said radiation over wavelengths within the range of visible and near infrared light.

* * * * *